United States Patent [19]

Aruffo et al.

[11] Patent Number: 5,709,859
[45] Date of Patent: Jan. 20, 1998

[54] MIXED SPECIFICITY FUSION PROTEINS

[75] Inventors: Alejandro A. Aruffo, Edmonds; Peter S. Linsley; Jeffrey A. Ledbetter, both of Seattle; Nitin K. Damle, Bellevue; H. Perry Fell, Jr., Redmond, all of Wash.

[73] Assignee: Bristol-Myers Squibb Company, New York, N.Y.

[21] Appl. No.: 645,522

[22] Filed: Jan. 24, 1991

[51] Int. Cl.$^6$ .......................... A61K 45/00; C07K 16/46
[52] U.S. Cl. ........................ 424/134.1; 424/136.1; 424/178.1; 435/69.7; 530/387.3; 530/388.22; 530/808; 530/866
[58] Field of Search .................... 530/387, 350, 530/402.3, 387.3, 388.2; 424/85.9, 134.7, 136.1, 178.1; 435/69.3

[56] References Cited

U.S. PATENT DOCUMENTS

| | | | |
|---|---|---|---|
| 4,816,567 | 3/1989 | Cabilly et al. | 530/387 |
| 5,109,123 | 4/1992 | Reinherz et al. | 536/27 |

FOREIGN PATENT DOCUMENTS

| | | | |
|---|---|---|---|
| 0346078 | 6/1989 | European Pat. Off. | A61K 39/395 |
| 0365837 | 9/1989 | European Pat. Off. | A61K 37/02 |
| 0408859 | 5/1990 | European Pat. Off. | A61K 37/02 |
| WO 90/13300 | 11/1990 | WIPO | A61K 31/70 |
| 9116437 | 10/1991 | WIPO | C12N 15/62 |

OTHER PUBLICATIONS

Dietsch, M. T. et al., J. Leukocyte Biology 56:444–452, "Coengagement of CD2 with LFA–1 or VLA–4 by bispecific ligand fusion proteins primes T cells to respond more effectively to T cell receptor–dependent signals", Oct. 1994.

Dietsch, M. T. et al., J. Immunol. Methods 162:123–132, "Bispecific receptor globulins, novel tools for the study of cellular interactions", 1993.

Polte, T. et al., "Full length vascular cell adhesion molecule 1 (VCAM–1)," Nucl. Acids Res. 18(19):5901, 1990.

Springer, T. et al. Nature 346:425–434, 2 Aug. 1990, Adhesion Receptors of the Immune System.

Alberts, B. et al. (ed.) Mol. Biol. of the Cell, 1983 pp. 190–194.

Hynes, R.O. Cell 48:549–554, 1987, "Integrins: A Family of Cell Surface Receptors."

*Primary Examiner*—Thomas M. Cunningham
*Attorney, Agent, or Firm*—Joseph M. Sorrentino

[57] ABSTRACT

Mixed specificity fusion proteins capable of binding to cellular adhesion molecules have been produced. The fusion proteins contain a polypeptide region, such as an IgG constant region, operatively attached to at least two binding regions each of which corresponds to either an extracellular domain of a cell surface receptor for cellular adhesion molecules, or a variable region of an antibody directed to a cellular adhesion molecule.

A method of inhibiting inflammation is a patient is disclosed in which the present fusion proteins are administered to a patient to inhibit the attachment of inflammatory cells to vascular endothelium.

A method of inhibiting metastasis is disclosed in which the present fusion proteins are administered to a patient to inhibit the metastasis of responsive tumor cells.

22 Claims, 3 Drawing Sheets

MIXED SPECIFICITY FUSION PROTEINS

TECHNICAL FIELD OF INVENTION

The present invention is directed to mixed specificity fusion proteins capable of binding to cellular adhesion receptors, as well as their synthesis and use to inhibit inflammatory reactions and to inhibit cellular metastasis in a patient.

BACKGROUND OF INVENTION

Cellular organization of various differentiated tissues and organs depend on cell-surface interactions both with molecules on the surface of apposing cells and with extracellular matrix components and soluble proteins. The interplay between various cell-surface molecules and those contributed by the surrounding extracellular environment primarily regulates functional expression of various cellular components of the immune system: the leukocytes which predominantly include lymphocytes, monocytes and polymorphonuclear neutrophils. Genetic programs of individual leukocytes dictate the expression of an array of distinct surface molecules, many of them characterizing individual steps in the maturation or differentiation pathways of these leukocytes. These surface molecules can be classified into two main functional categories. The first category consists of cognitive receptors which fulfill cognitive functions related to the process of immune recognition such as T-cell antigen receptor or B-cell surface immunoglobulin molecules, or those which serve as receptors for molecules regulating growth and differentiation of leukocytes such as various cytokine receptors. The second category includes surface molecules, also known as adhesion receptors, which mediate intercellular adhesion and also that between cells and the extracellular constituents of the surrounding environment. Certain molecules can function as adhesion receptors as well as in signal transduction during cellular activation (Springer T. A., 1990, Nature 346:425–434; Osborn L, 1990, Cell 62:3–6; Hynes, R. O., 1987, Cell 48:549–554; Hemler, M. E., 1988, Immunol. Today 9:109–113; Patarroyo, M., and Makgoba, M. W., 1989, Scand. J. Immunol. 30:129–164; Moller, G. Editor, 1990, Immunol. Rev. 114:1–217).

The ability of circulating leukocytes to migrate across the vascular endothelial lining of the blood vessels (extravasation) is critical for homeostasis and also for effective host responses to infectious organisms and tumors. Lymphocytes continuously recirculate from blood into various lymphoid organs providing immunological surveillance and also serving to disseminate regionally stimulated lymphocytes to distant sites. During diverse inflammatory events, other leukocytes such as neutrophils and monocytes also migrate into lymphoid and nonlymphoid tissues. The leukocyte specificity of extravasation during inflammation likely assures the accumulation of leukocyte subsets appropriate to the particular stage and nature of the inflammatory response. Leukocyte extravasation is controlled in pan by specific interactions with vascular endothelial cells via specific adhesion receptors (Osborn L, 1990, Cell 62:3–6). There are at least three distinct classes of adhesive molecules that leukocytes employ during their adhesive interactions: a) integrins including LEC-CAMS/Selectins (ELAM-1, LAM-1/Leu8/TQ1, and GMP140/PADGEM); b) those belonging to the immunoglobulin superfamily which include CD2(LFA-2), CD3/TCR, CD4, CD8, CD28, CD44, CD54 (ICAM-1), ICAM-2, CD58 (LFA-3), VCAM-1,B7; and c) Class I and II MHC (See above cited articles).

The adhesion receptors which belong to the integrin family controlling intercellular interactions have been the focus of intensive investigations because of their active role in linking the extracellular environment with the cytoskeleton. Recently, at least ten different structurally related cell surface heterodimeric (alpha and beta complexes) molecules have been defined as integrins and further classified into subfamilies (Springer T. A., 1990, Nature 346:425–434; Hynes, R. O., 1987, Cell 48:549–554; Moller, G. Editor, 1990, Immunol. Rev. 114.:1–217). Each subfamily has a unique beta subunit, designated integrin beta1 (CD29), integrin beta2 (CD18), and integrin beta3 (CD61), each of which can associate with multiple alpha subunits, each with at least one di-valent cation binding site. The beta subunits are 37% to 49% identical to one another and alpha subunits are 25% to 46% identical. The integrin family includes receptors for extracellular matrix components such as fibronectin, laminin, vitronectin, and collagen which recognize Arg-Gly-Asp in their ligands and utilize the beta1 or beta3 subunits (Springer T. A., 1990, Nature 346:425–434; Hynes, R. O., 1987, Cell 48:549–554; Hemler, M. E., 1988, Immunol. Today 9:109–113; Patarroyo, M., and Makgoba, M. W., 1989, Scand. J. Immunol. 30:129–164; Moller, G. Editor, 1990, Immunol. Rev. 11.4:1–217).

There are at least six distinct alpha subunits alpha1 (CD49a), alpha2 (CD49b), alpha3 (CD49c), alpha4 (CD49d), alpha5 (CD49e), and alpha6 (CD49f) capable of associating with beta1 (CD29). The beta1 integrins are expressed on many nonhematopoietic and leukocyte cell types and are thought to play an active role in tissue organization by binding to extracellular matrix components found in many tissues and in the basement membranes underlying muscles, nervous system, epithelium and endothelium. While the expression of many beta1 integrins on leukocytes requires consistent activation, their expression on nonhematopoietic cells does not (Hemler, M. E., 1988, Immunol. Today 9:109–113; Patarroyo, M., and Makgoba, M. W., 1989, Scand. J. Immunol. 30:129–164). The complexity of the integrin family has been increased by the discovery of novel beta subunits beta3 (CD61), beta4 and beta5 that can associate with alpha 4, alpha 6, and alpha V subunits (Springer T. A., 1990, Nature 346:425–434; Hemler, M. E., 1988, Immunol. Today 9:109–113). This combinatorial use of alpha and beta subunits confers considerable diversity in ligand recognition and also helps regulate communications between the inside and outside of the cell.

The beta 2 integrin subfamily is by far the most influential family of adhesive molecules in regulating not only the adhesive interactions of leukocytes with other cells but also the subsequent funtional effects of interacting leukocytes (Springer T. A., 1990, Nature 346:425–434; Patarroyo, M., and Makgoba, M. W., 1989, Scand. J. Immunol. 30:129–164). It consists of a 95 kilodalton beta2 subunit (CD18) which is capable of noncovalently associating with three distinct alpha subunits: 177 kilodalton CD11a forming LFA-1 complex, 160 kilodalton CD11b forming MAC-1 complex and 150 kilodalton CD11c forming GP150/beta2 complex. Unlike the expression of beta1 and beta3 integrins which is quite broad, the expression of beta2 integrins (CD18) is restricted to the cells of hematopoietic origin. While the expression of CD11b/CD18 and CD11c/CD18 integrins was predominantly confined to the cells of monomyeloid sublineage, the CD11a/CD18 is expressed on all mature leukocytes and its expression is further increased upon activation and differentiation of these leukocytes. Certain types of chronically stimulated cytolytic T cells and natural killer cells also express the CD11c/CD18 complex in addition to CD11a/CD18. Although the expression of CD11b/CD18 (MAC-1) is primarily confined to the monomyeloid lineage, most natural killer (NK) cells and a minor population within CD8+T sublineage also express CD11b/CD18 on their surface. The alpha chains of the beta 2 integrin subfamily are structurally more homologous to each other than to those of other integrin subfamilies (Springer T. A., 1990, Nature 346:425–434; Hynes, R. O., 1987Cell 48:549–554; Moller, G. Editor, 1990, Immunol. Rev. 114:1–217).

The changes in the expression of various beta2 integrins due to activation appears to be governed also by their preordained genetic programs. On neutrophils and monocytes, stimulation with a number of factors including calcium ionophore, phorbol esters, fMLP, GM-CSF, TNF, C5a, PDGF, LTB4 or even increases in ambient temperature (hyperthemia) rapidly (minutes) results in significantly increased surface expression of both CD11b/CD18 and CD11c/CD18 without appreciable change in the levels of expression of CD11a/CD18 (LFA-1). In contrast, on lymphoid cells (both T and B) which express only CD11a/CD18, longer duration (hours) of activation is required to increase expression of CD11a/CD18 required, perhaps due to the fact that there are intracellular storage pools for CD11b/CD18 and CD11c/CD18 in myeloid cells. No such storage pools for CD11a/CD18 have been demonstrated for CD11a/CD18 in leukocytes expressing this complex (Moller, G. Editor, 1990Immunol. Rev. 114:1–217). The rapidity with which CD11b and CD11c surface expression is increased following stimulation of myeloid cells may reflect translocation of pre-formed CD11b/CD18 and CD11c/CD18 from their intracellular storage pools to the cell-surface rather than active synthesis of these molecules. In contrast, upregulation of expression of CD11a/CD18 on lymphoid cells following activation requires active transcription of both CD11a and CD18 genes (Springer T. A., 1990,Nature 346:425–434; Patarroyo, M., and Makgoba, M. W., 1989, Scand. J. Immunol. 30:129–164; Moller, G. Editor, 1990, Immunol. Rev. 114:1–217).

Although the expression of beta2/CD18 integrins is restricted to the bone marrow-derived cells, that of their ligands/counter-receptors ICAM-1 (CD54) and ICAM-2, both members of the Ig superfamily, is not restricted to hematopoietic cells. Both ICAM-1 and ICAM-2 can be expressed by a wide variety of somatic cells in addition to cells of lymphomyeloid lineages. Although the receptor:ligand relationship between CD11a/CD18 (LFA-1) and ICAM-1 or ICAM-2 has been well established, interaction of CD11a/CD18 complex with ICAM-2 is of lower avidity than that with ICAM-1. Moreover, ICAM-2 is constitutively expressed by many somatic cells and its expression remains unchanged by stimulation with various proinflammatory mediators. In contrast, the expression of ICAM-1 is very tightly regulated on most cells and is readily increased on nonhematopoietic cells in response to proinflammatory stimuli such as IL-1 or TNF. Once these stimuli are removed from the environment the expression of ICAM-1 on these cells rapidly decreases. The induction of ICAM-1 in various cells is largely regulated at the mRNA level and unlike that of CD11b and CD11c, preformed intracellular reserves of ICAM-1 have not been observed (Springer T. A., 1990, Nature 346:425–434; Patarroyo, M., and Makgoba, M. W., 1989, Scand. J. Immunol. 30:129–164; Moller, G. Editor, 1990, Immunol. Rev. 114:1–217). The expression of ICAM-1 on lymphoid cells is also very tightly regulated and is controlled by the state of maturation of lymphocytes, in that only lymphocytes which have had prior antigenic exposure (primed or memory lymphocytes) express ICAM-1 on their surface. However, upon stimulation naive or virgin lymphocytes do begin to express ICAM-1 on their surface, a change usually associated with the maturation event. It would suffice to state that the degree of expression of ICAM-1 on various leukocytes is controlled by their respective states of maturation (Springer T. A., 1990, Nature 346:425–434; Moller, G. Editor, 1990, Immunol. Rev. 114:1–217).

The CD11b/CD18 molecule also exhibits ability to bind to ICAM-1. In addition, this molecule is also utilized in binding to Arg-Gly-Asp sequences within iC3b, factor X of the clotting cascade, and fibrinogen, each perhaps contributing to the activation of neutrophils. Although the expression of CD11c/CD18 is upregulated during activation of neutrophils and monocytes, its interacting ligand still remains elusive (Moller, G. Editor, 1990, Immunol. Rev. 114:1–217).

Both the initiation and maintenance of various immune functions are regulated by intercellular adhesive interactions between leukocytes and other interacting cells (predominantly vascular endothelial cells and various antigen-presenting cells such as dendritic cells or epidermal langerhans cells) and beta2 integrins play a pivotal role in this process. The availability of murine monoclonal antibodies (mAb) directed at various cell-surface molecules has tremendously facilitated analysis of these intercellular interactions resulting in the functional definition and classification of various adhesion molecules described above. The original demonstration of the active participation of beta2 integrins came from the studies on the interaction of cloned cytolytic T cells with their targets; an effort which also yielded knowledge about the involvement of CD2 (LFA-2) and its ligand CD58 (LFA-3). Mab directed at CD11a/CD18 (LFA-1), CD2, or CD58 significantly inhibited cytolytic activities of cloned killer T cells. Subsequently, mAb-inhibition studies were also extended to various other model systems. Thus, mAb directed at these three sets of molecules were able to inhibit antigen-specific immune functions of lymphocytes such as antigen-presentation, antigen-induced helper T cell activation, lymphokine production, and T-helper:B-cell collaboration resulting in the production of antibody molecules (Springer T. A., 1990, Nature 346:425–434). In addition, mAb directed at CD11a/CD18 were also able to inhibit the lysis of tumor cells by activated NK cells or lymphokine-activated killer cells. Thus, almost all facets of lymphoctye functions appear to involve the participation of beta2 integrins and mAb to these molecules are capable of inhibiting the development of various lymphocyte functions by interfering in the adhesive interactions featuring beta2 integrins and their counter-receptors ICAM-1 and ICAM-2 on apposing cells. (Springer T. A., 1990, Nature 346:425–434).

The beta2 integrins are also intricately involved in the functions of neutrophils and also other granulocytes such as eosinophils, basophils and mast cells. Predominant function of polymorphonuclear leukocytes is to sense the existence of inflammatory foci and in response to the inflammatory stimuli emigrate across the endothelial barrier to the inflammed sites to carry out the scavenger role. As a result, interaction of neutrophils with vascular endothelial cells are considered crucial in host defense against infections and also the subsequent repair process. Neutrophils are the predominant leukocytes at the inflammed site with the peak of emigration occurring within the first several hours after the onset of inflammation. Within 12–24 hours, however, mononuclear cells including lymphocytes and monocyte/macrophages become the most abundant cell in the inflammatory infiltrate (Moller, G. Editor, 1990, Immunol. Rev. 114:1–217; Bevilacqua, M. P. and Gimbrone Jr, M. A., 1987, Seminars in Thrombosis and Hemostasis 14:425–433; Harlan, J. M., 1987, Seminars in Thrombosis and Hemostatis 14:434–444; Pober, J. S., 1988, Am. J. Pathol. 133:426–433). The active role of beta2 integrins in the process of adhesion to endothelial cells and subsequent transendothelial emigration of phagocytes into the inflammed tissue has been illustrated in patients suffering with the leukocyte adhesion deficiency (LAD) wherein leukocytes have reduced or absent surface expression of beta2 integrin heterodimers resulting in profound defects in phagocyte emigration due to the inability of leukocytes to adhere to endothelial cells when stimulated. As a result, LAD patients demonstrate absence of pus at sites of bacterial infection and consequently suffer recurrent and life-threatening bacterial infections. Stimulated leukocytes employ CD11a/CD18 and CD11b/CD18 molecules during their adherence to unstimulated ICAM-1 bearing endothelial cells. This interaction can be significantly inhibited by mAb directed at CD11a, CD11b or CD18 molecules. MAb 60.3 which is a murine IgG2a antibody directed at the CD18 molecule was one of the first mAb targeted at beta2 integrins and was shown to be one of the best, if not the best, mAb to block neutrophil-endothelial interactions (Springer T. A., 1990, Nature 346:425–434; Moller, G. Editor, 1990, Immunol. Rev. 114:1–217; Harlan, J. M., 1987, Seminars in Thrombosis and Hemostatis 14:434–444).

Upon stimulation endothelial cells express additional adhesion molecules of the LEC-CAM/Selectin family such as ELAM-1 and CD62/PADGEM/GMP-140 to strengthen this interaction (Springer T. A., 1990, Nature 346:425–434; Moller, G. Editor, 1990, Immunol. Rev. 114:1–217; Pober, J. S., 1988, Am. J. Pathol. 133:426–433) as a consequence of which neutrophils become less dependent on beta2 integrins for their adherence to endothelial cells. Despite their lowered dependence for adherence to endothelial cells, emigration of neutrophils across activated endothelium still requires active participation of beta2 integrins. Thus, although adherence to endothelial cells can be achieved via use of alternate adhesion receptors such as CD15 or LAM-1/Leu8/TQ1 molecules the expression of which is intact in LAD patients, the emigration across the endothelium is dependent on the contribution by beta2 integrins perhaps by modulating cytoskeletal elements via their beta2 integrin membrane anchors (Patarroyo, M., and Makgoba, M. W., 1989, Scand. J. Immunol. 30:129–164; Moller, G. Editor, 1990, Immunol. Rev. 114:1–217; Harlan, J. M., 1987, Seminars in Thrombosis and Hemostatis 14:434–444).

Although a vast majority of reports dealt with the inhibition of various adhesion-dependent functions of leukocytes in vitro by mAb directed at beta2 integrins, a few elegant studies have been carried out with anti-CD18 mAb in vivo in experimental animals and also in man. In mice, antibodies to the beta2 integrins have been shown to inhibit migration of lymphoid cells into lymph nodes and Peyer's patches, recruitment of monocytes and neutrophils to thioglycollate-elicited peritoneal exudates and thus, reducing the severity of peritonitis (Patarroyo, M., and Makgoba, M. W., 1989, Scand. J. Immunol. 30:129–164). Using isolated perfused lungs as a model system, pulmonary injury caused by phorbol ester-activated human neutrophils could be attenuated by mAb to beta2 integrin (Patarroyo, M., and Makgoba, M. W., 1989, Scand. J. Immunol. 30:129–164). Similarly, accumulation of neutrophils and proteinaceous contents of the plasma in inflamed skin lesions were shown to be reduced by anti-CD18 mAb, perhaps due to inhibition of both the adherence to endothelium and subsequent migration across into the extravascular tissue (Smith, C. W., Rothlein, R., Hughes, B. J., Mariscalco, M. M., Rudloff, H. E., Schmalsteig, F. C., and Anderson, D. C., 1988, J. Clin. Invest. 82:1746–1756; Smith, C. W., Marlin, S. D., Rothlein, R., Toman, C., and Anderson, D. C., 1989, J. Clin. Invest. 83:2008–2017; Vedder, N. B., Winn, R. K., Rice, C. L., Chi, E. Y., Arfors, K. E., and Harlan, J. M., 1990, Proc. Natl. Acad. Sci. USA, 87:2643–2646).

The monoclonal antibody MAb 60.3 directed at beta2 integrin (CD18) (Beatty, P. G., Ledbetter, J. A., Martin, P. J., Price, T. H., and Hansen, J. A., 1983, J. Immunol. 131:2913–2918) was shown to reduce organ injury and improve survival from hemorrhagic shock and resuscitation in rabbits by attenuating both the liver and gut injuries caused by generalized ischemia and reperfusion. The above tissue injury is considered to be the consequence of damage caused by activated neutrophils to the endothelium and the surrounding tissue (Vealder, N. B., Winn, R. K., Rice, C. L., Chi, E. Y., Arfors, K. E., and Harlan, J. M., 1990, Proc. Natl. Acad. Sci. USA, 87:2643–2646). In another model, myocardial injury (myocardial infarction) caused by activated neutrophils in ischemic and reperfused dogs was significantly reduced by the anti-CD18 mAb 60.3 (Patarroyo, M., and Makgoba, M. W., 1989, Scand. J. Immunol. 30:129–164; Moller, G. Editor, 1990, Immunol. Rev. 114:1–217; Beatty, P. G., Ledbetter, J. A., Martin, P. J., Price, T. H., and Hansen, J. A., 1983, J. Immunol. 131:2913–2918). In humans, mAb to the CD11a/CD18 (LFA-1) was reported to prevent allogeneic graft-failure in HLA-mismatched bone marrow transplantation.

Mab 60.3 recognizes an epitope on the CD18 (beta2 integrin) molecule (Beatty, P. G., Ledbetter, J. A., Martin, P. J., Price, T. H., and Hansen, J. A., 1983, J. Immunol. 131:2913–2918) which is a constituent of all the three beta2 integrins (CD11a, CD11b, CD11c) critically involved in all functions mediated via beta2 integrins (Springer T. A., 1990, Nature 425–434; Patarroyo, M., and Makgoba, M. W., 1989, Scand. J. Immunol. 30:129–164; Moller, G. Editor, 1990, Immunol. Rev. 114:1–217; Smith, C. W., Rothlein, R., Hughes, B. J., Mariscalco, M. M., Rudloff, H. E., Schmalsteig, F. C., and Anderson, D. C., 1988, J. Clin. Invest. 82:1746–1756; Vealder, N. B., Winn, R. K., Rice, C. L., Chi, E. Y., Arfors, K.-E., and Harlan, J. M., 1990, Proc. Natl. Acad. Sci. USA, 87:2643–2646). Hence, mAb 60.3 can be used to inhibit adhesion-dependent functions of leukocytes which differentially make use of distinct beta2 integrins. This mAb is one of the first, if not the first, anti-CD18 mAb described (Patarroyo, M., and Makgoba, M. W., 1989, Scand. J. Immunol. 30:129–164; Beatty, P. G., Ledbetter, J. A., Martin, P. J., Price, T. H., and Hansen, J. A., 1983, J. Immunol. 131:2913–2918) and its use in both in vitro and in vivo studies has been well-documented (Patarroyo, M., and Makgoba, M. W., 1989, Scand. J. Immunol. 30:129–164; Moller, G. Editor, 1990, Immunol. Rev. 114:1–217). This mAb is highly regarded among anti-CD18 antibodies in its ability to inhibit a plethora of leukocyte functions. For application in humans, however, the use of a mouse antibody presents several immunologic difficulties. The present inventors have therefore produced novel mixed specificity fusion proteins derived from human protein genes which are applicable for use in inhibiting inflammation and metastasis in humans.

SUMMARY OF THE INVENTION

The present invention is directed to substantially pure chimeric molecules and their use to inhibit inflammatory and metastatic processes. These chimeric molecules are fusion proteins that contain at least two separate binding regions. Each of these regions has binding specificity for a cellular adhesion molecule. Each of these binding regions has the specificity of a different cell surface receptor extracellular domain or represents the variable region of an antibody directed to an adhesion molecule. The binding regions are operatively attached to a polypeptide to produce the chimeric molecule of the present invention.

One class of molecules of the present invention are immunoglobulin-like fusion proteins having a mixed specificity containing such binding regions. The immunoglobulin constant region of these fusion proteins can substantially correspond to a constant region of IgG. Binding regions of the fusion proteins can comprise binding portions of the extracellular domains of cell surface receptors, such as ELAM-1, GMP140, and ICAM-1. Specific fusion proteins contemplated by the present invention include a fusion protein of a human IgG constant region attached to regions of the extracellular domains of ELAM-1 and GMP140, a fusion protein of an IgG constant region attached to regions of the extracellular domains of ICAM-1 and ELAM-1, a fusion protein of an IgG constant region attached to regions of the extracellular domains of ELAM-1 and VCAM-1, and a fusion protein of an IgG constant region attached to regions of the extracellular domains of ICAM-1 and GMP140.

Compositions of the fusion proteins of the present invention are further contemplated, together with methods of inhibiting inflammation and metastasis in a patient by administering a therapeutically effective amount of the fusion protein of the present invention to the patient.

Figure 1:
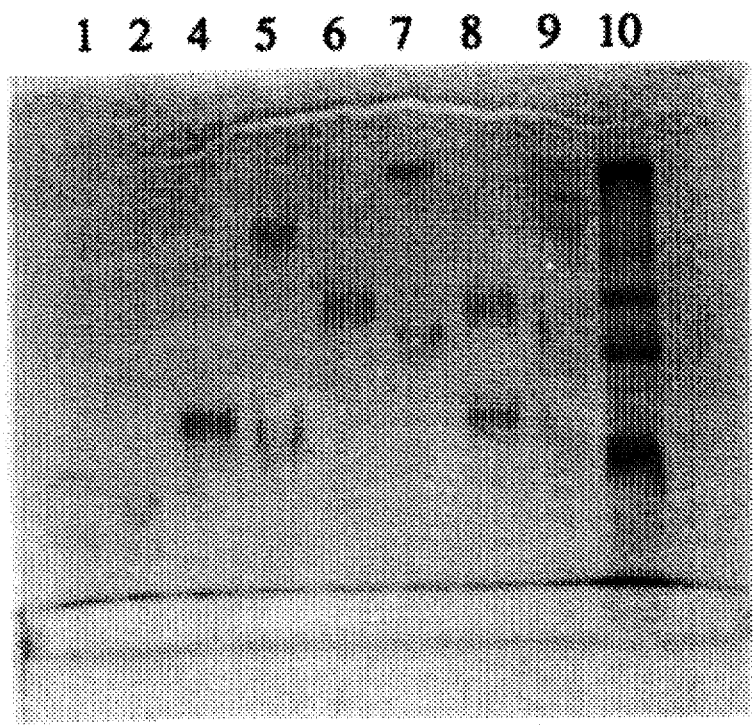
FIG. 1 illustrates the SDS-PAGE banding patterns for supernatants from transfected cells under reducing and nonreducing conditions (lane 1 and 2); supernatants from cells transfected with a plasmid encoding the GMP140-IgG fusion protein under reducing and nonreducing conditions (lane 3 and 4); supernatants from cells transfected with a plasmid encoding the ELAM-1-IgG fusion protein under reducing and nonreducing conditions (lane 5 and 6); supernatants from cells cotransfected with a mixture of plasmids encoding the GMP140-IgG and ELAM-1-IgG fusion proteins under reducing and nonreducing conditions (lane 7 and 8); and molecular weight markers (lane 9).

Panel B illustrates a SDS-PAGE analysis of the fractions obtained from the hydroxyapatite separation of Panel A.

Five-fraction groups, starting at fraction 1 and extending to fraction 50, were pooled and concentrated on a sephacryl protein A matrix. The concentrated fractions were applied to SDS-PAGE and the protein bands resolved.

DESCRIPTION OF PREFERRED EMBODIMENTS

The present invention is directed to mixed specificity fusion proteins that are capable of binding to cellular adhesion proteins. Particular fusion proteins of the present invention contain a polypeptide or an immunoglobulin-like protein region, such as an IgG constant region, operatively linked, or attached, to at least two specific binding regions. Each binding region preferably corresponds to either a variable region of an antibody directed to an adhesion molecule or a region of the extracellular domain of a cell surface receptor, such as ELAM-1, VCAM-1, GMP140 and ICAM-1. A particularly preferred antibody variable region is the variable region corresponding to the specificity of mAb 60.3 which is directed against beta 2 integrin (CD 18).

As used herein the term "extracellular domain" refers to a region of the extracellular portion of a cell surface receptor that retains binding specificity for a cellular adhesion molecule. Such an extracellular domain is capable of inhibiting binding between target cells such as neutrophils and vascular endothelium.

As used herein, the term "cellular adhesion molecule" refers to specific inflammatory cell surface molecules that are recognized and bind to vascular endothelium and/or granulocytes.

As used herein, the term "operatively attached" refers to the linkage of groups in a manner such that the binding affinity of the group is not inhibited by the attachment.

As used herein, the term "IgG constant region" refers to domains of the gamma chain of the IgG molecule that are adjacent to the variable region that corresponds to the first 107 amino acids of the gamma chain or fragments thereof. The four domains within the gamma chain constant region are designated $CH_1$, H, $CH_2$, and $CH_3$. $CH_1$ is adjacent to the variable region and encompasses amino acid residues 114 through 223. H (hinge; residues 224–245) is adjacent to $CH_1$ and contains the cysteine residues that form the disulfide bonds which covalently link the two immunoglobulin heavy chains. $CH_2$ is adjacent to the hinge and encompasses amino acid residues 246 through 361, followed by $CH_3$ which contains amino acid residues 362 through 496.

The extracellular domains of at least two different cell surface receptors are thus fused in the present invention to give hybrid fusion proteins having multiple specificities and functional properties. The fusion proteins are capable of binding to natural ligands on target cells, such as endothelial cells and neutrophils, and blocking adhesion and/or cellular activation. The proteins of the present invention are thus contemplated to be effective in blocking neutrophil-mediated endothelial cell injury, such as in ischemia-reperfusion, by blocking CD18 mediated neutrophil aggregation and adherence to endothelium.

The mixed specificity receptor fusion proteins of the present invention are preferably directed against the neutrophil cell surface proteins responsible for neutrophil-endothelial binding, and thus they can block the binding of neutrophils to endothelium.

In a preferred embodiment, the fusion proteins of the present invention are produced by fusing the cDNA fragments encoding the extracellular domains of the endothelial and granulocyte surface receptors responsible for neutrophil-endothelium binding, such as ICAM-1/ICAM-2, VCAM-1, ELAM-1 and GMP140, to a genomic fragment encoding the human IgG constant region. Combinations of these constructs are then transfected into mammalian cells. The mixed specificity receptor-immunoglobulin fusion proteins are thereby assembled in these cells and secreted side by side with the single specificity immunoglobulin fusion proteins. In the present invention mixed specificity fusion proteins, such as ICAM-1/ELAM-1, ICAM-1/ GMP-140, VCAM-1/GMP-140 etc., have been produced and can be tested alone and in combination for their ability to bind neutrophils and alleviate reperfusion injury.

Fusion proteins of the present invention are preferably produced by the fusion of human proteins and, as such, would be less immunogenic than non-human monoclonal antibodies that may have related specificity to one or more adhesion molecules. The multiple specificity of these fusion proteins enables the simultaneous binding of several of the neutrophil proteins responsible for neutrophil-endothelial binding, and thus will be potent blockers of the neutrophil-endothelial adhesion that is associated with reperfusion injury and inflammation.

Preferred embodiments of the present invention are the mixed specificity fusion proteins described herein, the pharmaceutically acceptable salts thereof and related variants thereof. The phrase "pharmaceutically acceptable salts", as used herein, refers to non-toxic alkali metal, alkaline earth metal and ammonium salts used in the pharmaceutical industry, including the sodium, potassium, lithium, calcium, magnesium and ammonium salts and the like that are prepared by methods well-known in the art. The phrase also includes non-toxic acid addition salts that are generally prepared by reacting the compounds of this invention with a suitable organic or inorganic acid. Representative salts include the hydrochloride, hyrdrobromide, sulfate, bisulfate, acetate, oxalate, valerate, oleate, laurate, vorate, benzoate, lactate, phosphate, tosylate, citrate, maleate, fumarate, succinate, tartrate and the like.

Compositions of the present invention contain mixed specificity fusion proteins, as described hereinabove, together with a pharmaceutically acceptable carrier. As used herein, the term "pharmaceutically acceptable carrier" refers to a physiologically tolerable, non-toxic material in which the fusion proteins of the present invention can be dissolved or dispersed. Illustrative pharmaceutically acceptable carriers can be solid or liquid materials and can include water, saline, phosphate-buffered saline, Ringer's solution, dextrose, cornstarch, lipid emulsions and the like.

The fusion proteins and compositions of the present invention can be effectively utilized in a method for inhibiting inflammation in a patient. A therapeutically effective amount of a mixed specificity fusion protein, as described herein, is adminstered to a patient for a time period sufficient to a ameliorate or inhibit inflammatory processes and/or reactions in the patient by inhibiting the attachment of inflammatory cells, such as neutrophils, to vascular endothelium.

The fusion proteins and compositions of the present invention can also be effectively utilized for the inhibition of metastasis in a patient. Colon carcinoma cells are known to have glycosylated surface proteins which are recognized by cellular receptors such as VCAM-1 and ICAM-1. In a method of the present invention, a therapeutically effective amount of a mixed specificity fusion protein, as described herein, is administered to a patient for a time period sufficient to inhibit the metastasis of responsive tumor cells.

The present invention is further described by the following Examples which are intended to be illustrative and not limiting.

EXAMPLE 1

Preparation of ELAM-1/GMP140 Fusion Proteins

Expression plasmids containing cDNA fragments encoding the complete extracellular domain of ELAM-1 and the four amino terminal domains of the GMP140 protein fused to a genomic fragment encoding the human IgG constant region were mixed in equal amounts and cotransfected into COS monkey cells by the DEAE-dextran method of Seed, B. and Aruffo, A., 1987, Proc. Natl. Acad. Sci. USA, 84:3365–3369.

Twenty four hours after transfection the cells were washed with phosphate-buffered saline (PBS, 5 milliliters (ml)/100 mm dish), and the serum-containing medium (Dulbeccos's Modified Eagle's medium (DMEM) plus 10% fetal bovine serum (FBS)) was replaced with serum-free medium (DMEM, 10 ml/100 mm dish). Four days following transfection additional serum-free DMEM was added to the transfected cells (10 ml/dish) and six days later the COS cell supernatant was harvested and cellular debris were removed by low speed centrifugation.

The recombinant proteins obtained were analyzed by sodium dodecyl sulfate-polyacrylamide gel electrophoresis (SDS-PAGE). The results shown in FIG. 1 illustrate the banding for proteins obtained from mock-transfected COS cells (control), COS cells transfected with DNA encoding the ELAM-1 immunoglobulin fusion protein (ELAM-1-IgG) or COS cells transfected with DNA encoding the GMP140 immunoglobulin fusion protein (GMP140-IgG). It can be seen that the supernatant obtained from the COS cells transfected with the mixture of DNAs contain three proteins corresponding to the ELAM-1-IgG and the GMP140-IgG homodimeric fusion proteins and the ELAM-1/GMP140 mixed specificity receptor fusion protein.

Analysis of the proteins under reducing conditions showed two bands corresponding to the ELAM-1-IgG and the GMP140-IgG monomeric fusion proteins, respectively. This result indicates that the mixed specificity ELAM-1/GMP140 receptor fusion protein is assembled by the transfected cell and held together by disulfide bonds located within the hinge region of the IgG Fc region.

EXAMPLE 2

Purification Of ELAM-1/GMP140 Fusion Protein

Figure 2A:
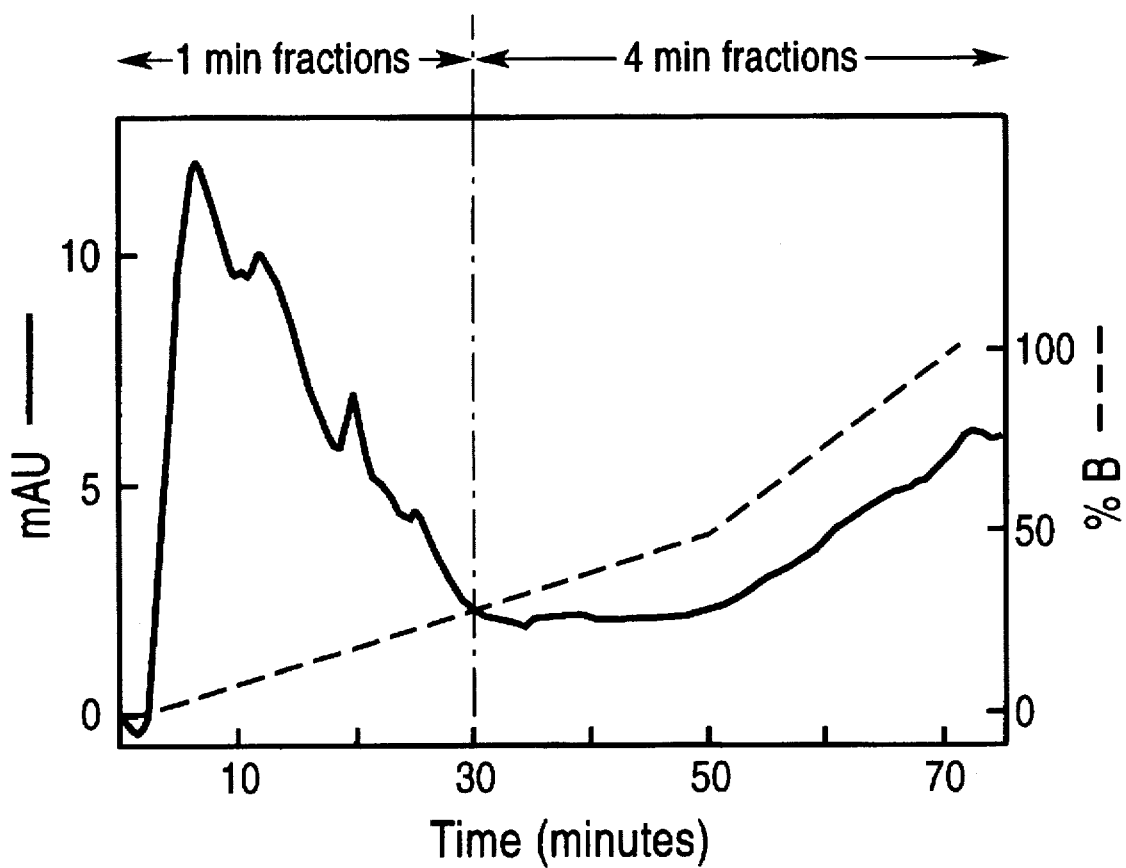
FIGS. 2A and B illustrates the purification of the ELAM-1/GMP140 IgG fusion protein. Panel A shows an elution profile for the separation of COS cell supernatant proteins upon a hydroxyapatite column. Elution is with a $KH_2PO_4/K_2HPO_4$ (pH6.8) gradient from 10 mM to 350 mM, at a flow rate of 1 ml/min., 1 ml fractions were collected.
Figure 2B:
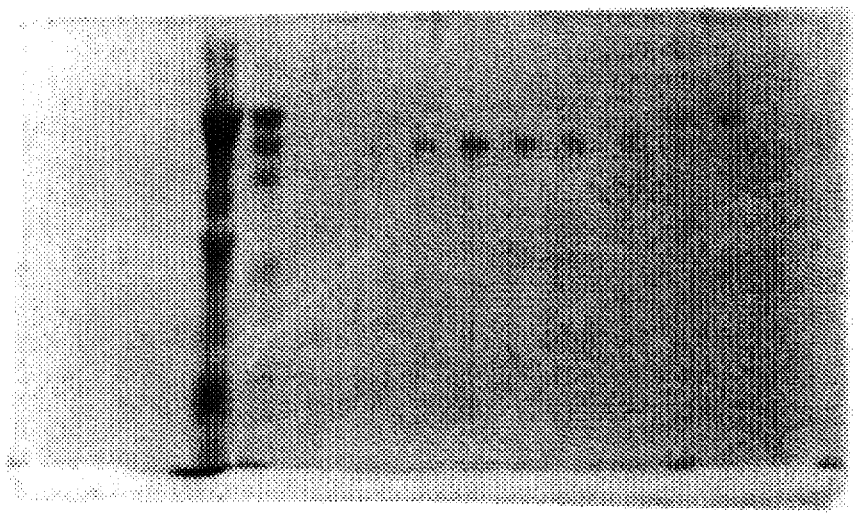

The ELAM-1/GMP140 mixed specificity receptor proteins in the crude COS cell supernatant described in EXAMPLE 1 were purified by passage over a hydroxyapatite column. Material bound to the column was then eluted using a $KH_2PO_4/K_2HPO_4$ (pH 6.8) gradient starting at 10 mM and ending at 350 mM with a flow rate of 1 ml/min. The elution profile is shown in FIG. 2A. Groups of five one-milliliter fractions (5 ml) at a time were removed during the elution (from Fraction 1 to Fraction 50), pooled, concentrated on a sephacryl protein A matrix and analyzed by SDS-PAGE (FIG. 2B). The results show that the mixed specificity ELAM1/GMP140 IgG heterodimer can be separated from the ELAM-1-IgG and the GMP140-IgG homodimers.

The foregoing description and Examples are intended as illustrative of the present invention, but not as limiting. Numerous variations and modifications may be effected without departing from the true spirit and scope of the present invention.

We claim:

1. A substantially pure heterodimeric molecule comprising two chimeric chains, each of said chains comprising an immunoglobulin heavy chain constant domain and a binding region fir a cellular adhesion molecule wherein each chain has a binding region for a different cellular adhesion molecule and wherein the two chains of said heterodimeric molecule are associated via the immunoglobulin heavy chain constant domains.

2. The heterodimeric molecule according to claim 1 wherein each binding region has the specificity of a different cell surface receptor extracellular domain.

3. The heterodimeric molecule according to claim 1 wherein at least one binding region has the specificity of a variable region of an antibody directed against a cell adhesion molecule.

4. The heterodimeric molecule according to claim 3 wherein the binding region corresponds to the specificity of the variable region of mAb 60.3.

5. The heterodimeric molecule according to claim 3 wherein said heterodimeric molecule comprises an immunoglobulin constant region operatively attached to two binding regions, each binding region comprising an extracellular domain for a different cell surface receptor for cell adhesion molecules.

6. The heterodimeric molecule according to claim 5 wherein said immunoglobulin constant region substantially corresponds to a constant region of human IgG.

7. The heterodimeric molecule according to claim 5 wherein one binding region comprises an extracellular domain of ELAM-1.

8. The heterodimeric molecule according to claim 5 wherein one binding region comprises an extracellular domain of GMP140.

9. The heterodimeric molecule according to claim 5 wherein one binding region comprises an extracellular domain of ICAM-1.

10. The heterodimeric molecule according to claim 5 wherein one binding region comprises an extracellular domain of VCAM-1.

11. The heterodimeric molecule according to claim 5 comprising a fusion protein of an leg constant region attached to regions of the extracellular domains of ELAM-1 and GMP140.

12. The heterodimeric molecule according to claim 5 comprising a fusion protein of an IgG constant region attached to regions of the extracellular domains of ICAM-1 and ELAM-1.

13. The heterodimeric molecule according to claim 5 comprising a fusion protein of an IgG constant region attached to regions of the extracellular domains of ICAM-1 and GMP140.

14. The heterodimeric molecule according to claim 5 comprising a fusion protein of an leg constant region attached to regions of the extracellular domains of VCAM-1 and GMP140.

15. A pharmacological composition comprising a heterodimeric molecule comprising two chimeric chains, each of said chains comprising an immunoglobulin heavy chain constant domain and a binding region for a cellular adhesion molecule wherein each chain has a binding region for a different cellular adhesion molecule and wherein the two chains of said heterodimeric molecule are associated via the immunoglobulin heavy chain constant domains.

16. The composition according to claim 15 wherein at least one binding region comprises a variable region of an antibody directed against a cell adhesion molecule.

17. The composition according to claim 15 wherein said heterodimeric molecule comprises an immunoglobulin constant region operatively attached to two binding regions, each binding region comprising an extracellular domain of a different cell surface receptor for cell adhesion molecules.

18. The composition according to claim 17 wherein said immunoglobulin constant region substantially corresponds to a constant region or human IgG.

19. The composition according to claim 17 wherein one binding region comprises an extracellular domain of ELAM-1.

20. The composition according to claim 17 wherein one binding region comprises an extracellular domain of GMP140.

21. The composition according to claim 17 wherein one binding region comprises a extracellular domain of ICAM-1.

22. The composition according to claim 17 wherein one binding region comprises a extracellular domain of VCAM-1.

* * * * *